US00PP16391P3

(12) United States Plant Patent

Murakami et al.

(10) Patent No.: US PP16,391 P3
(45) Date of Patent: Mar. 28, 2006

(54) *CALIBRACHOA* PLANT NAMED 'SUNBELBUSTA'

(50) Latin Name: ***Calibrachoa* sp.**
Varietal Denomination: Sunbelbusta

(75) Inventors: Yasuyuki Murakami, Gamo-gun (JP); Takeshi Kanaya, Omihachiman (JP)

(73) Assignee: Suntory Flowers Limited, Tokyo (JP)

( * ) Notice: Subject to any disclaimer, the term of this patent is extended or adjusted under 35 U.S.C. 154(b) by 115 days.

(21) Appl. No.: 10/810,496

(22) Filed: Mar. 25, 2004

(65) Prior Publication Data

US 2005/0216988 P1 Sep. 29, 2005

(51) Int. Cl.
*A01H 5/00* (2006.01)

(52) U.S. Cl. ..... Plt./263
(58) Field of Classification Search ..... Plt./263, Plt./356
See application file for complete search history.

(56) References Cited

U.S. PATENT DOCUMENTS

| | | | |
|---|---|---|---|
| PP9,557 | P | 5/1996 | Suzuki et al. |
| PP9,754 | P | 12/1996 | Suzuki et al. |
| PP10,279 | P | 3/1998 | Murakami |
| PP10,355 | P | 4/1998 | Murakami |
| PP11,558 | P | 10/2000 | Murakami |

FOREIGN PATENT DOCUMENTS

| | | |
|---|---|---|
| JP | PBR 7229 | 6/1999 |
| JP | PBR 7231 | 6/1999 |

OTHER PUBLICATIONS

GTITM UPOVROM Citation for 'Sunbelbusta' as per CA PBR 04–4071; Feb. 27, 2004.*
GTITM UPOVROM Citation for 'Sunbelbusta' as per AU PBR 200160; May 20, 2004.*
Explanation of Publications of Japanese PBR Registrations and family documents thereof.
Suntory Flowers Ltd., "Flower & Green, the newest catalog 2004" Published 2003, With Explanation.
Suntory Ltd., Japan, Flower & Green, the newest catalog 2002 Published 2002, With Explanation.
Jackson & Perkins wholesale, Inc., USA, "The 2004 Suntory Collection" Published 2003, With Explanation.
Pineae Greenhouses, Inc., USA, "Pineae Peak Performers featuring the 2004 Suntory Collection" Published 2003, With Explanation.
Moerheim New Plant bv., USA, "The Suntory Collection 2004" Published 2003, With Explanation.
Ramm Botanicals Pty Ltd., AU., "The Colour Wave Collection 2003–4 . . . beautiful flowering plants" Published 2002, With Explanation.

* cited by examiner

*Primary Examiner*—Kent Bell
(74) *Attorney, Agent, or Firm*—Christie, Parker and Hale, LLP

(57) ABSTRACT

Disclosed herein is a new and distinct variety of *Calibrachoa* plant having an outwardly spreading growth habit. The *Calibrachoa* plant has abundant branching, and a great profusion of blooms, the whole plant remaining in bloom for a considerable period of time. The flowers are single and very small, the petals having a vivid purple color with deep purple vein. The inside color of the corolla throat is vivid yellow with brilliant yellow-green and the outside of the corolla tube is strong purple with dark redish-purple. The plant exhibits high resistance to heat, cold, rain and disease.

2 Drawing Sheets

Botanical/commercial classification: *Calibrachoa* sp./ *Calibrachoa* Plant.
Varietal denomination: cv. 'Sunbelbusta'.

BACKGROUND OF THE VARIETY

The present invention relates to a new and distinct variety of *Calibrachoa* plant, botanically known as *Calibrachoa* sp., which originated from crossing of a *Calibrachoa* hybrid variety called 'CHBS05' as the female parent and 'CHBS07' as the male parent.

The female parent 'CHBS05' (unpatented) used in the crossing of 'Sunbelbusta' is a strain of our breeding lines, having an erect growth habit. It has small single flowers, the petals having a vivid red-purple color.

The male parent 'CHBS07' (unpatented) used in the crossing of 'Sunbelbusta' is a strain of our breeding lines, having a decumbent growth habit. It has small single flowers, the petals having violet color.

In July 1998, crossing of 'CHBS05' as the female parent and 'CHBS07' as the male parent was conducted at Yokaichi-shi, Shiga-ken, Japan. In October 1998, seedlings were obtained from that crossing. These seedlings were grown in pots in glasshouses and were evaluated. One seedling was selected in view of its growth habit, flower size and color in October 1999. That seedling was propagated by cutting and a trial was carried out by flower potting and bedding from April to October 2000. The botanical characteristics of that plant were then examined, using similar varieties 'Sunbelribu' (unpatented) and 'Sunbelkubu' (U.S. Plant Pat. No. 10,279) for comparison. As a result, it was concluded that this *Calibrachoa* plant is distinguishable from any other variety whose existence is known to us, and is uniform and stable in its characteristics. The new variety of *Calibrachoa* plant was named 'Sunbelbusta'.

In the following description, the color-coding is in accordance with the Horticultural Colour Chart of The Royal Horticultural Society, London, England (R.H.S. Colour Chart).

SUMMARY OF THE VARIETY

This new variety is unlike any *Calibrachoa* commercially available as evidenced by the following unique combinations of characteristics.

1. Outwardly spreading growth habit with abundant branching.
2. Great profusion of blooms with the entire plant remaining in bloom for a considerable period of time.
3. The flowers are single and very small. The apex shape of petal is acute. The petal color is vivid purple (near R.H.S. N81A) with deep purple (near R.H.S.83A) vein.
4. The plant has a high resistance to rain, cold, heat and disease.

The new variety 'Sunbelbusta' differs from the similar variety 'Sunbelribu' in the following points.

1. The spreading area of 'Sunbelbusta' is larger than that of 'Sunbelribu'.
2. The internode length of 'Sunbelbusta' is shorter than that of 'Sunbelribu'.
3. The flower diameter of 'Sunbelbusta' is larger than that of 'Sunbelribu'.
4. The petal color of 'Sunbelbusta' is vivid purple (near R.H.S.N81A) with deep purple (near R.H.S.83A) vein, while that of 'Sunbelribu' is vivid purple (near R.H.S.N87A).
5. Inside color of the corolla throat of 'Sunbelbusta' is vivid yellow (near R.H.S. 7B) with brilliant yellowish green (near R.H.S. N199A) vein. That of 'Sunbelribu' is vivid greenish-yellow (near R.H.S.151C).
6. Outside color of the corolla tube of 'Sunbelbusta' is strong purple (R.H.S.83D) with dark reddish-purple (near R.H.S.79A). That of 'Sunbelribu' is light yellow-green (near R.H.S.1C).

The new variety 'Sunbelbusta' differs from the similar variety 'Sunbelkubu' in the following points.

1. The growth habit of 'Sunbelbusta' is outwardly spreading, while that of 'Sunbelkubu' is decumbent.
2. The plant height of 'Sunbelbusta' is higher than that of 'Sunbelkubu'.
3. The leaf length of 'Sunbelbusta' is longer than that of 'Sunbelkubu'.
4. The petal color of 'Sunbelbusta' is vivid purple (near R.H.S.N81A) with deep purple (near R.H.S.83A), while that of 'Sunbelkubu' is vivid purple (R.H.S.N81A).
5. Inside color of the corolla throat of 'Sunbelbusta' is vivid yellow (near R.H.S. 7B) with brilliant yellowish green (near R.H.S. N199A) venation, while that of 'Sunbelkubu' is brillant greenish yellow (near R.H.S.5C).
6. Outside color of the corolla tube of 'Sunbelbusta' is strong purple (R.H.S.83D) with dark reddish purple (R.H.S.79A), while that of 'Sunbelkubu' is pale yellow green (R.H.S.1D).
7. The apex shape of the petal of 'Sunbelbusta' is acute, while that of 'Sunbelkubu' is obtuse.

This new variety of *Calibrachoa* plant 'Sunbelbusta' was asexually reproduced by the use of cuttings of Yokaichi-shi, Shiga-ken, Japan, and homogeneity and stability thereof were confirmed. The instant plant retains its distinctive characteristics and reproduces true to type in successive generations.

BRIEF DESCRIPTION OF THE PHOTOGRAPHS

The depicted plants have been reproduced by the use of cuttings and were photographed during April 2003 while growing outdoors in 20 cm wall pots at an age of approximately 4 months at Yokaichi-shi, Shiga-ken, Japan.

DESCRIPTION OF THE VARIETY

Figure 1:
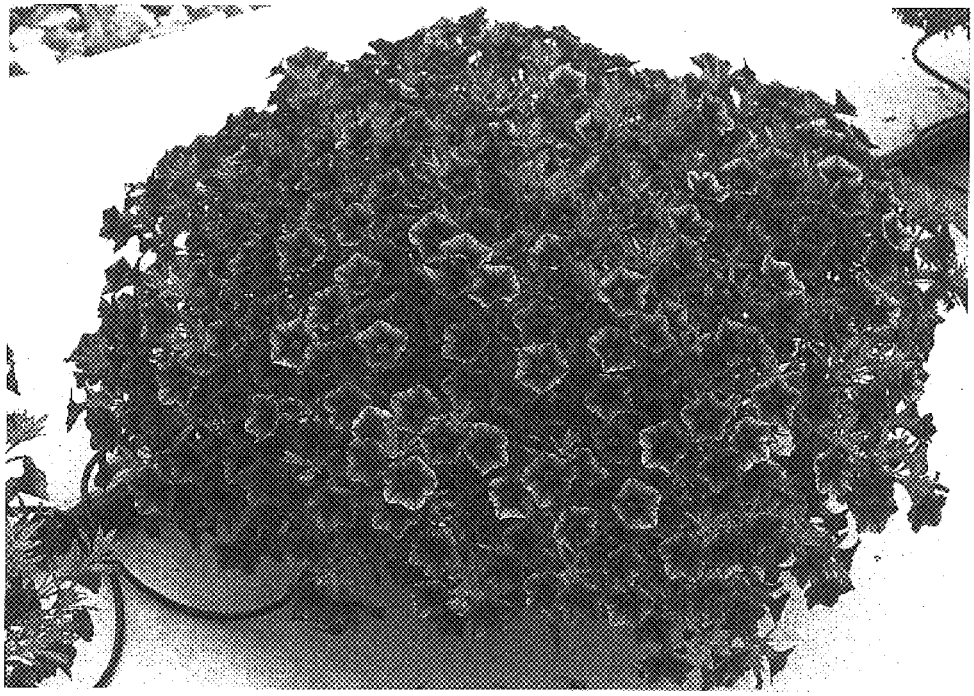
FIG. 1 is a photograph of a typical plant of the new variety of *Calibrachoa* plant 'Sunbelbusta' while growing in a pot.
Figure 2:
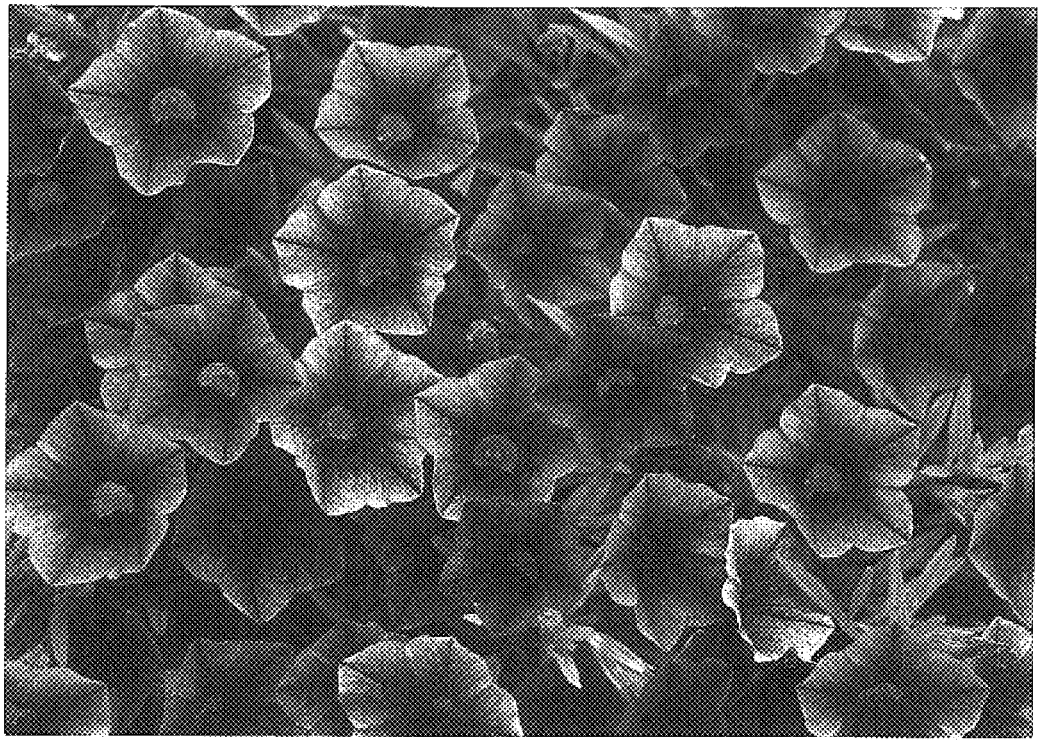
FIG. 2 is a close view of flowers and leaves of the new variety of *Calibrachoa* plant 'Sunbelbusta'.

The botanical characteristics of the new and distinct variety of *Calibrachoa* plant named 'Sunbelbusta' are as follows when observed during September at Yokaichi-shi, Shiga-ken, Japan, at an age of approximately 9 months.

Plant:
- *Growth habit.*—Outwardly spreading.
- *Plant height.*—Approximately 23.8 cm.
- *Spreading area of plant.*—Approximately 49.0 cm.
- *Blooming period.*—April to late October in the southern Kanto area, Japan. The plant shape does not change throughout this period.

Stem:
- *Length.*—Approximately 30.0 cm.
- *Thickness.*—Approximately 1.8 mm.
- *Pubescence.*—Normal.
- *Branching.*—Abundant branching, especially secondary branches.
- *Internode length.*—Approximately 0.9 cm.
- *Color.*—Near R.H.S. 165A (grayish yellow brown).

Leaf:
- *Whole shape.*—Lanceolate. The apex shape is acute, and the base shape is attenuate.
- *Length.*—Approximately 4.4 cm.
- *Width.*—Approximately 1.0 cm.
- *Color.*—Upper side is near R.H.S. 137C (moderate yellow green). Lower side color is near R.H.S. 146C (moderate yellow green).
- *Thickness.*—Approximately 0.5 mm.
- *Pubescence.*—Normal.

Buds:
- *Shape.*—Cylindrical.
- *Length.*—Approximately 2.0 cm.
- *Diameter.*—Approximately 4.0 mm.
- *Color.*—Towards apex, near R.H.S. N81B; Base — near R.H.S. 151D; Venation — near R.H.S. 79A.

Flower:
- *Facing direction.*—Horizontal.
- *Type.*—Single.
- *Shape.*—Funnel-shaped, with five-fissures.
- *Lobation.*—Medium.
- *Waviness of petal.*—Weak.
- *Diameter.*—Approximately 3.5 cm.
- *Depth.*—Approximately 2.7 cm.
- *Tube length.*—Approximately 1.8 cm.
- *Throat diameter.*—Distal end — Approximately 0.8 cm.
- *Tube diameter.*—Proximal end — Approximately 2.0 mm.
- *Petals.*—Width — Approximately 1.3 cm. Length from throat — Approximately 1.4 cm. Shape — Broadly obtrullate. Shape of petal tip — Acute. Margin — Entire. Texture — Smooth. Color — Lower surface, near R.H.S. N81B with near R.H.S. 79A venation.

*Color.*—Petal; near R.H.S. N81A (vivid purple) with near R.H.S. 83A (deep purple) vein. Bottom color of the corolla throat; near R.H.S. 7B (vivid yellow) with near R.H.S. N199A (brilliant yellowish green) vein. Outside color of the corolla tube; near R.H.S. 83D (strong purple) with near R.H.S. 79A (dark redish purple) vein. Upper color of the corolla throat — near R.H.S. 83A.

*Reproductive organs.*—1 normal pistal and 5 normal stamens. The stigma is club-shaped and near R.H.S.144C (strong yellow green) in coloration. The style is approximately 6 mm in length and near R.H.S. 144D (light yellow green) in coloration. The ovary is near R.H.S. 165A (grayish reddish purple) in coloration. The stamens commonly are of variable length from approximately 5.7 to 9.1 mm. Pollen is formed in a quantity that is typical of *Calibrachoa* sp. and is near R.H.S.9B (vivid yellow) in coloration.

*Fertility.*—Fertile, but self-incompatible.

*Peduncle.*—Approximately 0.7 mm in diameter and approximately 1.8 cm in length. The texture is smooth. Color is near R.H.S. 144B.

*Seeds.*—Near R.H.S. N186A (strong red) in coloration, approximately 0.6 mm in diameter, and generally round. The quantity is typical of *Calibrachoa* sp.

Sepals:

*Shape.*—Narrow elliptic.

*Apex shape.*—Obtuse.

*Base.*—Fused.

*Margin.*—Entire.

*Length.*—Approximately 1.4 cm.

*Width.*—Approximately 3.0 mm.

*Color.*—Upper and lower surfaces near R.H.S. 137C.

*Calyx.*—Narrow. 5 sepals fused at the base.

Physiological and ecological characteristics: High resistance to cold, heat, rain and disease such as Powdery mildew. The resistance to heat and rain is very strong.

Blooming: This new variety of *Calibrachoa* plant is most suitable for flower bedding and potting, particularly in hanging pots or planters. Pinching of old blossoms will enhance the formation of new blossoms.

It is claimed:

1. A new and distinct variety of *Calibrachoa* plant named 'Sunbelbusta', substantially as herein illustrated and described.

* * * * *